United States Patent [19]

Muller et al.

[11] 4,342,951

[45] Aug. 3, 1982

[54] SERVOELECTRIC MICROMANIPULATOR FOR MOVEMENT ON SPHERICAL COORDINATES

[75] Inventors: Ortwin Muller; Klaus Biber, both of Aalen; Roland Schmauder, Oberkochen, all of Fed. Rep. of Germany; Manfred Spitznas, Encino, Calif.

[73] Assignee: Carl Zeiss-Stiftung, Oberkochen, Fed. Rep. of Germany

[21] Appl. No.: 102,334

[22] Filed: Dec. 11, 1979

[30] Foreign Application Priority Data

Dec. 16, 1978 [DE] Fed. Rep. of Germany ....... 2854514

[51] Int. Cl.³ ............................................. G05B 11/32
[52] U.S. Cl. .................................... 318/625; 318/628; 128/303 B; 128/305
[58] Field of Search ..................... 318/628, 625, 2, 54, 318/55, 59, 103; 128/303 R, 303 B, 305

[56] References Cited

U.S. PATENT DOCUMENTS

| | | | |
|---|---|---|---|
| 3,693,066 | 9/1972 | Friedman et al. | 318/628 |
| 3,771,037 | 11/1973 | Bailey, Jr. | 318/628 |
| 4,170,850 | 10/1979 | Horvath et al. | 318/628 |

FOREIGN PATENT DOCUMENTS 252000  11/1970  U.S.S.R. ............................... 128/303

*Primary Examiner*—J. V. Truhe
*Assistant Examiner*—Eugene S. Indyk
*Attorney, Agent, or Firm*—Hopgood, Calimafde, Kalil, Blaustein & Judlowe

[57] ABSTRACT

The invention contemplates a micromanipulator as for the manipulation of a vitrectomy instrument, wherein a single remotely operable control means is effective through three independent spherical-coordinate servoelectric drives to selectively control the operative end of the instrument, within an operating volume defined by spherical coordinates centered at a fixed point of origin; in a vitrectomy, the fixed point of origin is illustratively the point of surgical entry through the pars plana of the eye.

8 Claims, 5 Drawing Figures

SERVOELECTRIC MICROMANIPULATOR FOR MOVEMENT ON SPHERICAL COORDINATES

BACKGROUND OF THE INVENTION

This invention relates to a spherical-coordinate micromanipulator for the operating element of a vitrectomy instrument, wherein motion of the operating element is controllable in any desired direction of the coordinate system.

Vitrectomy is a new method of operation in the field of vitreous surgery. With respect to access or entry into the volume of the corpus vitreum, one distinguishes between "open sky vitrectomy" and "vitrectomy via pars plana". Vitrectomy through the pars plana makes use of special motorized instruments for the purpose of cutting the pathologically modified vitreous body into small pieces, and at the same time drawing them off. In detail, the present methods are described by H. D. Gnad in an article entitled, "The Present Status of Vitrectomy", published in *Klinische Monatsblatter fur Augenheilkunde*, 166 (1975), pages 817 to 825. And in the journal *"Archives of Ophthalmology"*, Volume 88, September 1972, pages 325 to 329, B. R. Straatsma et al. have described a spherical-coordinate micromanipulator for vitrectomy operations. The disadvantage of the known micromanipulator is that the movement of the vitrectomy instrument is carried out manually, without any auxiliary energy. For each of the three coordinate directions involved, a mechanical operating element is provided. This type of motion control is so cumbersome, due to the need for continuous change between the three operating elements, that the user can guide the vitrectomy instrument to the target point only after various manipulations and frequent change of the grip of the hand.

BRIEF STATEMENT OF THE INVENTION

The object of the present invention is to provide the surgeon with an improved micromanipulator which achieves simpler, more precise, and faster control of a vitrectomy instrument within the eye than has been previously the case, thus shortening the time to perform an operation, and making possible more difficult or more lengthy operations.

This object is achieved in accordance with the invention by providing independent remote-controlled electric servomotors for guided displacement in each of the three spherical coordinates of a vitrectomy instrument mounted to the micromanipulator. A single manual control element is preferably provided for determining displacement motion of the vitrectomy instrument, said element being capable of deflection in accordance with the direction of the spherical coordinates and of being located at any desired point separated from the instrument.

In one advantageous embodiment of the invention, the control element is developed as a control stick, one end of which carries a rotatable knob, and the other end of which is preferably cardanically mounted, being associated with electric signal transmitters which, upon deflection of the control stick within the degrees of freedom afforded by universal action of the support and upon turning of the rotatable knob, cause a predetermined and corresponding movement or speed of one or more of the servomotors, and thus of the vitrectomy instrument.

The servomotors are preferably embodied as DC motors, and a separate electric signal transmitter is preferably associated with each direction of rotation of each of the servomotors.

An electric switch is also preferably provided for selective reversal of the direction of rotation of the servomotors which serve the angular components $\alpha_1$ and $\alpha_2$ of the spherical coordinates.

The advantages obtained with the invention consist of ease and precision of handling, which leads to physical and mental relief for the surgeon.

DESCRIPTION OF A PREFERRED EMBODIMENT

One embodiment of the invention is shown by way of illustration in the drawing and will be described in further detail below. In the drawings.

Figure 1:
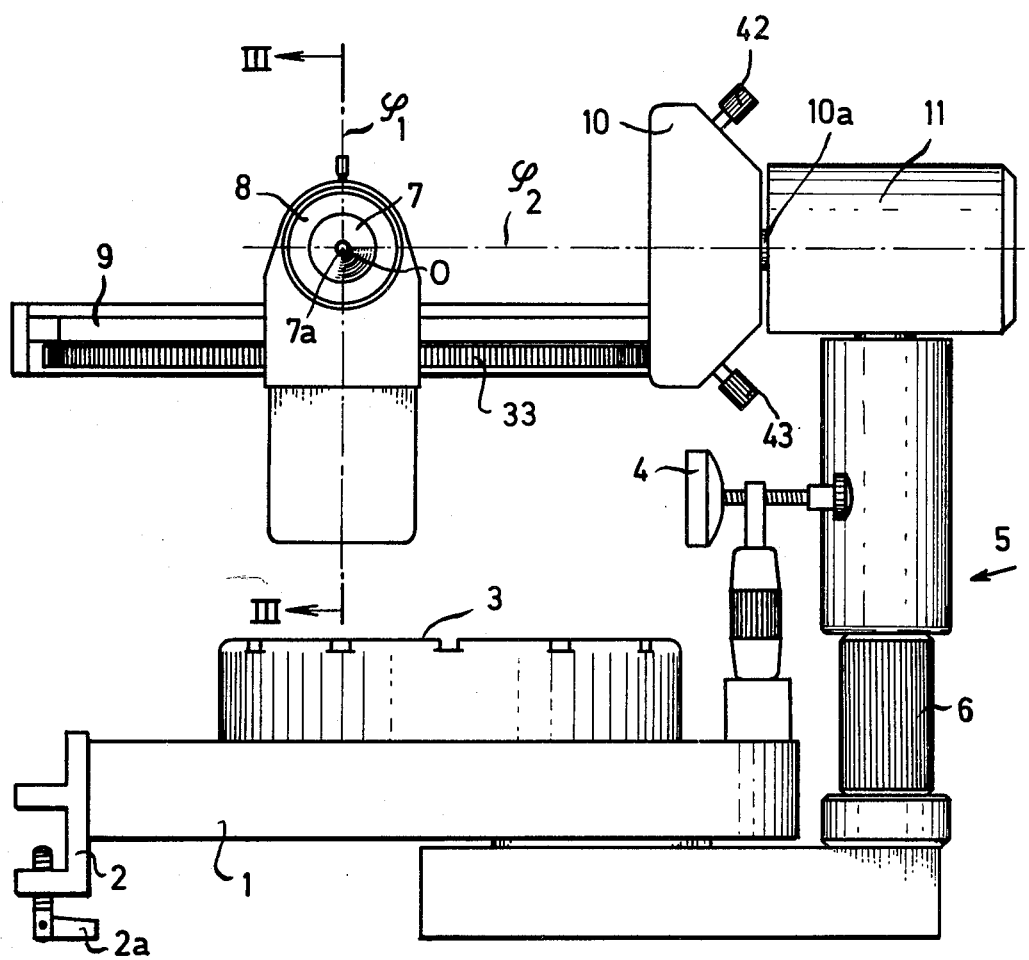
FIG. 1 is a side view of the instrument of the invention.
Figure 2:
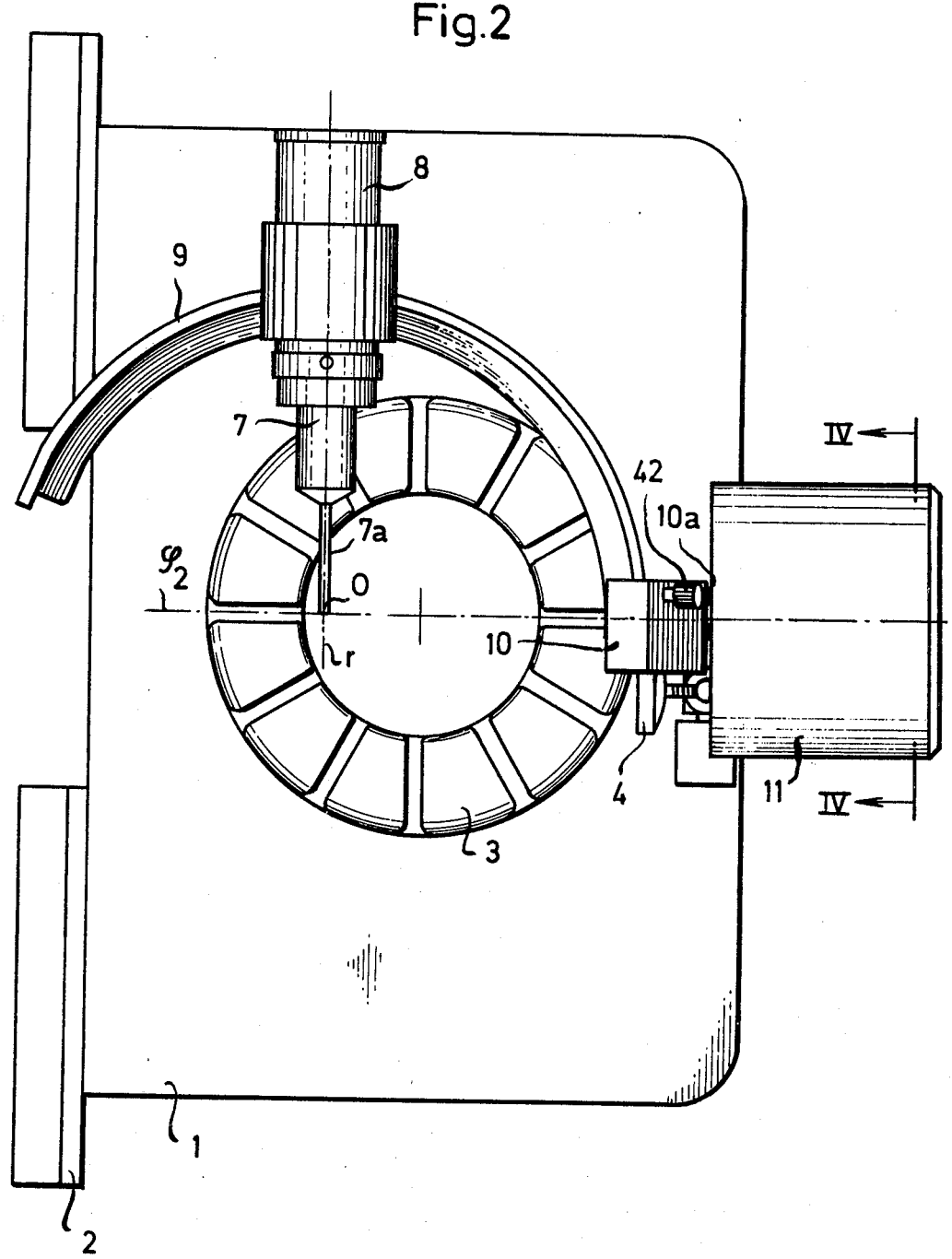
FIG. 2 is a top view of the instrument shown in FIG. 1.

Referring initially to FIGS. 1 and 2 of the drawings, an instrument base plate 1 is adapted to be connected via fastening means 2 to an operating table. Base plate 1 carries a head rest or support 3 and plurality of spaced clamping devices 4 for holding the head of the patient; for simplicity of illustration in FIGS. 1 and 2, only one of preferably three such clamping devices 4 has been shown. Compound-slide means of known type (not shown in detail) is mounted to the underside of base plate 1, and a supporting column 5 is mounted to the compound-slide means. The supporting column 5 contains vertical-adjustment means of known type, actuated by turning a knurled ring 6. It will be understood that the compounds-slide means and the vertical-adjustment means serve for set-up purposes, adapting the instrument to the eye of the patient before initiating an operation; during the operation, movement of the compound-slide means and of the vertical-adjustment means is blocked, as by means of clamp screws (not shown).

Figure 4:
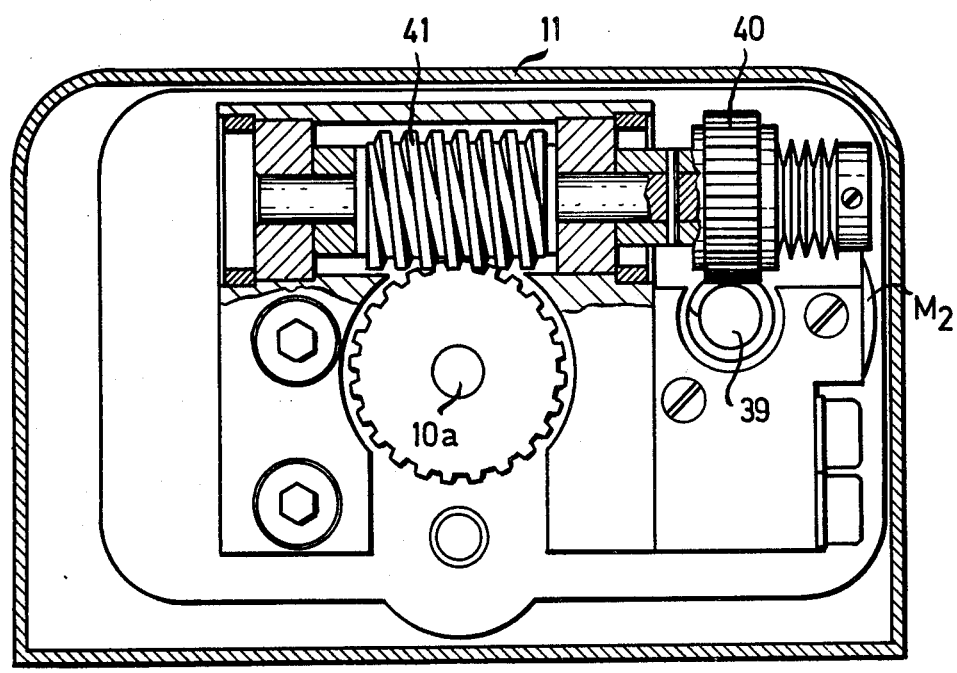
FIG. 4 is an enlarged section through another part, along the line IV—IV of FIG. 2.

Parts which permit movement of a vitrectomy instrument 7 on spherical coordinates are fastened to the upper part of column 5. The tip 7a of the vitrectomy instrument 7 is located in its zero (or null) position in the spherical center point 0 of the system. The instrument is clamped in a holding device 8 and can be motor-driven for displacement along its longitudinal axis (spherical coordinate r). The holding device 8 may also be motor-driven in arcuate displacement about the spherical center point 0, being guided by a circular-arc rail 9 for such motion; displacement along the circular arc represents the spherical coordinate $\alpha_1$. The arcuate rail 9 is carried by insertion of one of its ends in a holding device 10, in which it is fastened by a clamp screw 43; and the holding device 10 is mounted on a shaft 10a which, in turn, is journaled for rotation in a housing 11, carried at the upper end of column 5. The axis of rotary shaft 10a also passes through the spherical center point 0 and determines the spherical coordinate $\alpha_2$, and rotary displacement in the spherical coordinate $\alpha_2$ is effected by a servomotor $M_2$ arranged in the housing 11 (FIG. 4).

The instrument will be understood to be shiftable, using the compound-slide means, for transfer between an operating set-up for one eye of the patient to an operating set-up for the other eye of the patient. In making such a set-up change, the arcuate rail 9 and holding device 10 are 180°-reversed by such rotation of shaft 10a, the clamped end of rail 9 being released from clamp 43, and the opposite end of rail 9 being inserted into holding device 10, for clamping by means 42 at equal and opposite offset from the axis of shaft 10a.

Before commencing an operation, the spherical center point 0 of the micromanipulator is placed at the point of incision into the pars plana of the eye, whereby the penetration point is fixed during the operation, it being understood that the eye itself will have been held fixed by means not shown in the drawing. The point 7a of the vitrectomy instrument 7 can be lowered into the eye during the operation by means of the device of the invention, in which connection every point of the eye can be reached. For this purpose, a separate control-unit accessory contains suitable power-supply means, as well as means including a control stick 13 (FIG. 5) for remote control of the various motional-component drive motors of the micromanipulator.

Figure 3:
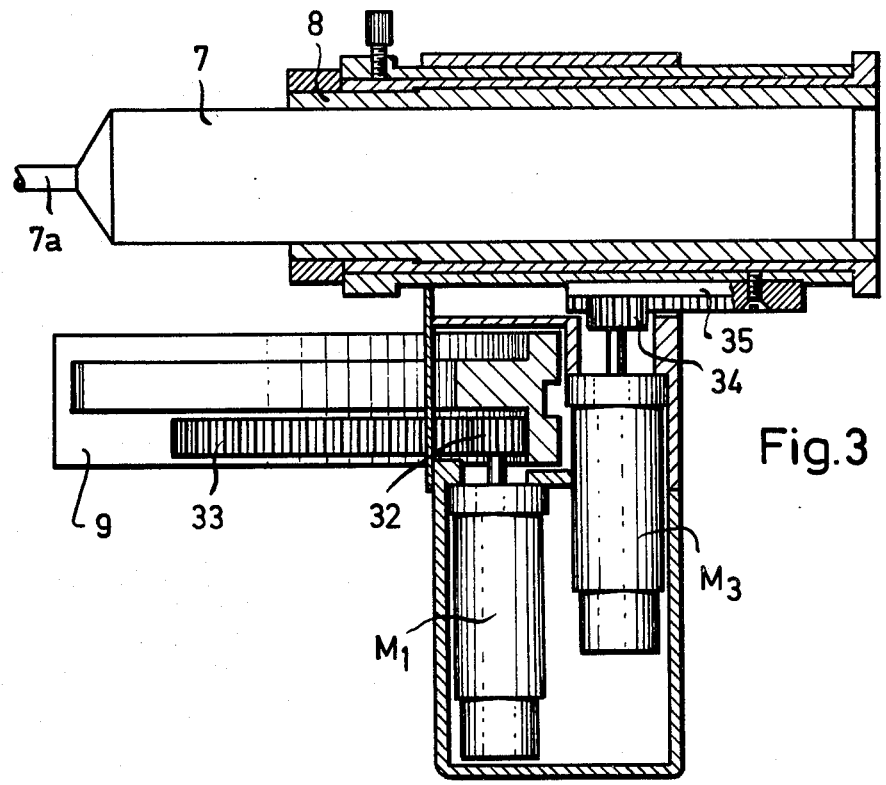
FIG. 3 is an enlarged section through part of the instrument, along the line III—III of FIG. 1.

The sectional view of FIG. 3 shows the arrangement of two of the servomotors, $M_1$ and $M_3$. A pinion 32 driven by servomotor $M_1$ engages the teeth of an arcuate-rack portion 33 of rail 9 and moves the instrument holder 8, in the coordinate $\alpha_1$ along the circular arc of rail 9. A pinion 34 driven by motor $M_3$ engages the rack 35 and moves the instrument holder 8 in its longitudinal direction, i.e., in the spherical coordinate r.

The sectional view of FIG. 4 shows the arrangement and manner of operation of servomotor $M_2$. A first worm 39 driven by motor $M_2$ meshes with a worm wheel 40 to drive another worm 41, and worm 41 meshes with a further worm wheel to drive the rotary shaft 10a, which is aligned through the spherical center point and effects rotary displacement of the holding device 10 for rail 9 in the spherical coordinate $\alpha_2$.

Figure 5:
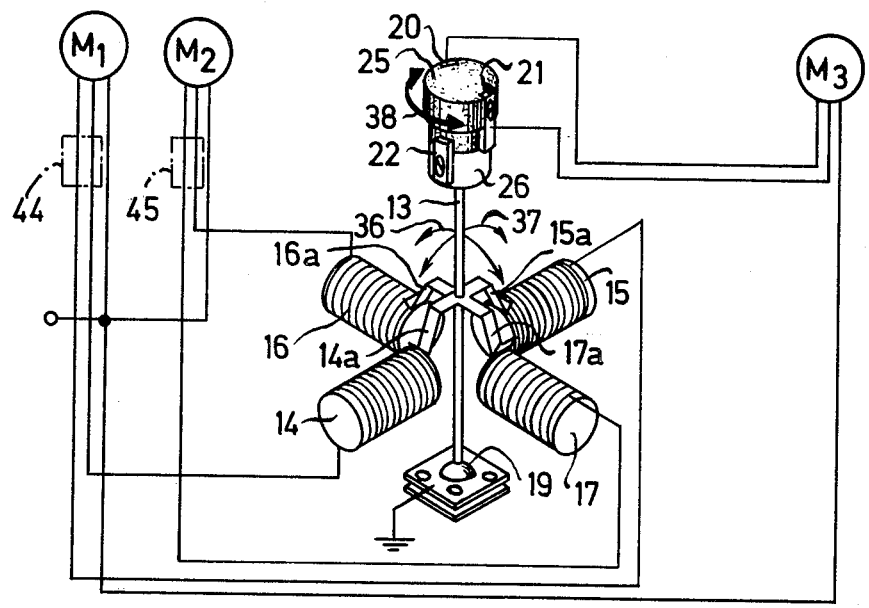
FIG. 5 is a schematic diagram of the operating element with its connection to the respective servomotors which effect the movement.

From FIG. 5, it can be seen how the movement of the instrument 7 is effected by actuation of the control stick 13. The control stick 13 is cardanically supported at 19 and is universally movable in the direction of the arrows 36-37, or diagonally in various component combinations of the directions 36-37, as desired. As a function of control-stick displacement, grounded wiper contacts 14a, 15a or 16a, 17a are pushed over resistors 14, 15 or 16, 17, fixedly mounted in quadrature symmetry about the spherical-center reference position of the control stick. The resistor pair 14-15 is connected for control of motor $M_1$ to effect $\alpha_1$-component displacement of holder 8 along rail 9, and the resistor pair 16-17 is connected for control of motor $M_2$ to effect $\alpha_2$-component displacement of rail-holding device 10. Upon turning a rotatable knob 25 at the upper end of stick 13, in the direction indicated by an arrow 38, and between limits 20-21 about a fixed stop 22, the servomotor $M_3$ is actuated—also via resistors (not shown)—to move the instrument in the coordinate direction r.

In the preferred embodiment of the invention, the speed of rotation of the motors and, thus, the speed of the vitrectomy instrument is proportional to the deflection of the control stick. The latter is therefore normally urged by springs to return to its zero or reference position, in which no motor motion takes place, and the instrument tip 7a remains at the point in space into which it was last displaced.

It is to be understood that the above-described example is merely illustrative of the many possible specific embodiments which can be devised to represent application of the invention by those skilled in the art. In particular, the invention also contemplates remote control of vitrectomy instrument 7 wherein deflection of the control stick is proportional to the position of the instrument, in which case it may not be desired to employ spring-return of control stick 13 and its knob 25 to its spherical-center reference position.

Although the servomotors $M_1$, $M_2$, $M_3$ are inherently bi-directional in their response to control-stick variation of their respective control resistances, it will be understood that selectively available polarity reversal is desirable for the angle-component control functions, $\alpha_1$, $\alpha_2$, as by operation of double-pole double-throw switches 44-45 (suggested by phantom outlines) in the resistance-control connections to motors $M_1$ and $M_2$. Availability of such polarity reversal will be seen as an aid to the surgeon who, in the course of optically observing the eye upon which he is operating, passes from direct to indirect ophthalmoscopy. For the user, the optical inversion of the image is thereby counteracted by an electric-control inversion.

From FIG. 3, it will be seen that the described functioning of the invention is achieved while also making it possible to easily remove movable parts of the micromanipulator for sterilization or other replacement purposes.

What is claimed is:

1. A micromanipulator for a surgical instrument, such as a vitrectomy instrument, said micromanipulator causing said surgical instrument to move in any desired direction in a spherical coordinate system, said micromanipulator being characterized in that the surgical instrument is guided in the micromanipulator by the operation of servomotors which are activated by manual control of a single, remote-controlled operation element which can be deflected in the direction of the spherical coordinates.

2. A micromanipulator according to claim 1, characterized by the fact that the operating element is a control stick (13) whose one end bears a rotatable knob (25) and whose other end is preferably cardanically supported (19) and that there are connected to the control stick (13) electric signal transmitters (14a, 15a, 16a, 17a) which, upon deflection of the control stick (13) in the directions permitted by the support (19) and upon rotatable of the turning knob (25), cause activation of the servomotors, and thus, a movement of the vitrectomy instrument which corresponds to the deflection or rotation of the control stick (13).

3. A micromanipulator according to claim 1, characterized by the fact that the servomotors ($M_1$, $M_2$) are DC motors, each servomotor having an electric signal transmitter (14, 15 and 16, 17, respectively) being associated with each direction of rotation.

4. A micromanipulator according to claim 3, characterized by the fact that an electric changeover switch (44, 45) is provided for reversing the direction of rotation of the servomotors ($M_1$, $M_2$) in the spherical coordinates $\alpha_1$ and $\alpha_2$.

5. A micromanipulator according to claim 3, characterized by the fact that the speed of rotation of the servomotors is directly proportional to the degree of deflection of the control stick.

6. The micromanipulator according to claim 5 characterized by the fact that the control stick is normally in a zero position where the servomotors are not activated unless there is manual deflection of the control stick.

7. A micromanipulator for power-assisted remote positioning control of a vitrectomy element within a three-dimensional volume having a spherical-coordinate center, said micromanipulator comprising a base frame, a vitrectomy-element holder having an elongate axis of vitrectomy-element support, and a spherical-coordinate system suspending and positioning said holder axis in constant alignment with said center; said system comprising (a) rectilineal holder-guide means extending along the holder axis and a first servomotor for linear positioning displacement of said holder along said axis, (b) an intermediate frame (9) including means for supporting said holder-guide means on and for rotation with respect to said intermediate frame, said rotation being about a first rotary axis orthogonal to said holder axis and through said center, (c) a second servomotor for angular positioning displacement of said guide means about said first rotary axis, (d) means on said base frame for supporting said intermediate frame for rotation about a second rotary axis in said base frame, said second rotary axis being orthogonal to both said holder axis and said first rotary axis and through said center, (e) a third servomotor for angular positioning displacement of said intermediate frame with respect to said base frame, and (f) a single manually operable control member mounted for universal action about a fixed center, a first selectively variable electrical element being carried by said control member and electrically coupled to said first servomotor, and second and third variable electrical elements being in orthogonal motion pick-off relation to universal-action displacement of said control member, said second and third electrical elements being electrically coupled to said second servomotor and to said third servomotor, respectively.

8. The micromanipulator of claim 7, in which said control member and said electrical elements are components of a separate unit having flexible electrical connection to said servomotors.

* * * * *